Figure 1:
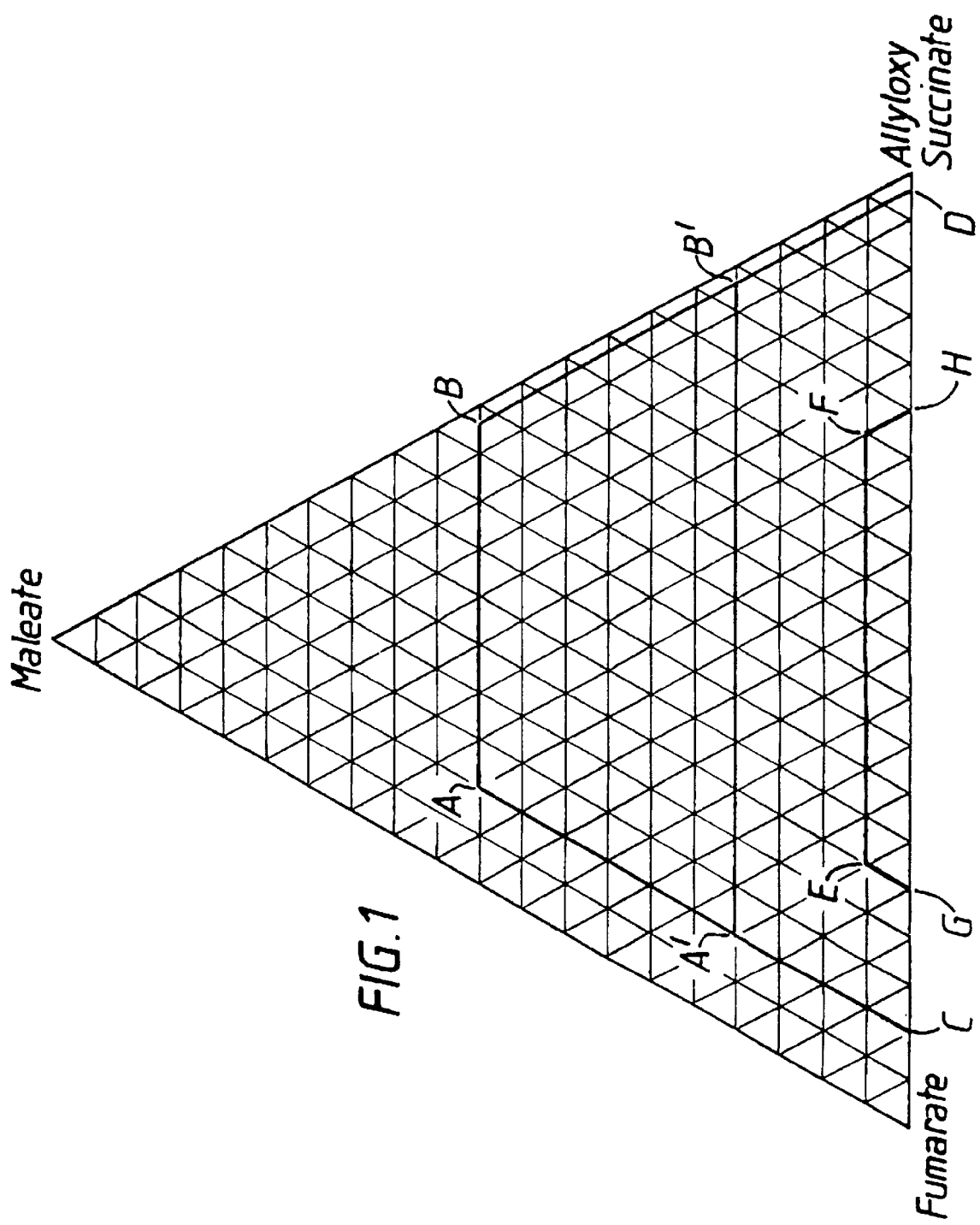

United States Patent [19]
Gracey et al.

[11] Patent Number: 6,130,275
[45] Date of Patent: Oct. 10, 2000

[54] MIXTURE OF ESTERS AND USE THEREOF

[75] Inventors: Benjamin Patrick Gracey, East Yorkshire; Christopher Hallett, Hertfordshire, both of United Kingdom; Robert Paul Klaasen, Amsterdam, Netherlands

[73] Assignee: BP Chemicals Limited, London, United Kingdom

[21] Appl. No.: 09/011,949

[22] PCT Filed: Jun. 27, 1997

[86] PCT No.: PCT/GB97/01741

§ 371 Date: Aug. 12, 1998

§ 102(e) Date: Aug. 12, 1998

[87] PCT Pub. No.: WO98/00387

PCT Pub. Date: Jan. 8, 1998

[30] Foreign Application Priority Data

Jun. 28, 1996 [GB] United Kingdom .................... 9613675
Nov. 27, 1996 [GB] United Kingdom .................... 9624679

[51] Int. Cl.$^7$ .................. C07C 67/03; C07C 69/527; C08L 67/08; C08F 222/26
[52] U.S. Cl. ................ 523/510; 525/7; 526/320; 560/217; 560/224; 560/225
[58] Field of Search ...................... 560/224, 225, 560/217; 523/510; 525/7; 526/320

[56] References Cited

FOREIGN PATENT DOCUMENTS

| 552715 | 4/1943 | United Kingdom . |
| WO 97/02229 | 1/1997 | WIPO . |
| WO 97/02230 | 1/1997 | WIPO . |

*Primary Examiner*—Patricia A. Short
*Attorney, Agent, or Firm*—Fay, Sharpe, Fagan, Minnich & McKee, LLP

[57] ABSTRACT

This invention relates to a composition comprising a mixture of a fumarate, maleate and 2-allyloxy-succinate esters falling within the area defined by points A, B, C, and D of a triangular chemical composition diagram (hereafter "TCCD") said points representing respectively the ranges of concentration of said maleate, fumarate and succinate in said composition, a process for preparing the same and the use thereof as a reactive diluent in a paint or coating formulation.

17 Claims, 1 Drawing Sheet

MIXTURE OF ESTERS AND USE THEREOF

This application is a continuation of international application No. PCT GB97/01741, filed Jun. 27, 1997.

This invention relates to a composition comprising a mixture of esters derivable from maleic and/or fumaric acid, anhydrides and alkyl esters thereof, a process for producing said mixture of esters and use of said ether esters as diluents in paint and polymer formulations.

One of the processes used hitherto to produce 2-substituted succinate esters is the combined transesterification and Michael addition reaction of an alcohol or a monoether of a polyoxyalkylene glycol as described in GB-A-552715 in which ether esters of hydroxysuccinic acid and unsaturated alcohols are prepared by reacting in a single step under anhydrous conditions an alkyl ester of maleic acid with an unsaturated alcohol in the presence of magnesium alkoxide as a catalyst. However, this method when repeated for instance with an octadienol/dimethyl maleate system using magnesium methoxide as described in GB-A-552715 gives products which have a deep red colour. It may be possible to overcome this colour problem in the products described in this prior art by distillation. However, such a distillation is unlikely to be practicable with the synthesis of esters contemplated in the present invention since these esters are all meant to have relatively low volatility and hence are not amenable to purification by distillation.

It has now been found that a mixture of esters can be produced in commercially viable yields and purity by using selective catalysts and process.

Accordingly, the present invention relates to a composition comprising a mixture of a fumarate, maleate and 2-allyloxy-succinate esters falling within the area defined by points A, B, C and D of a triangular chemical composition diagram (hereafter "TCCD") said points representing respectively the ranges of concentration of said maleate, fumarate and succinate in said composition.

Referring to the drawings:

FIG. 1 represents a chemical composition diagram according to the present invention.

Thus, the compositions of the present invention represented by the area defined by points A, B, C and D in the TCCD (see attached FIG. 1) suitably contain the fumarate, maleate and 2-allyloxy succinate esters in the following ranges in parts by weight percent (%): fumarate:maleate:2-allyoxysuccinate=3–90:0–50:10–97 and is preferably in the range from 3–97:0–20:10–97 represented by the area under points A', B', C and D, and more preferably in the range 25–75:0–5:25–75 represented by the area under points E, F G and H.

Specific examples of such mixed esters include:
 i. di-(2,7-octadienyl)maleate
    di-(2,7octadienyl)fumarate and
    2-(2,7-octadienoxy)di-(2,7-octadienyl)succinate
 ii. di-(2-ethylhexenyl)maleate
    di-(2-ethylhexenyl)fumarate and
    2-(2-ethylhexenoxy)di-(2-ethylhexenyl)succinate.

According to a further embodiment the present invention relates to a process for producing a mixture of esters (hereafter "MOE") represented by formula (I) said process comprising reacting a dicarboxylic compound selected from the group consisting of maleic acid, maleic anhydride, fumaric acid and the dialkyl ester of maleic or fumaric acid with a reactant alcohol R'O[CHR".CH$_2$O]$_x$H where x is 0 or an integer from 1–6 in the presence of a catalyst to form said MOE, the catalyst being selected from the group consisting of:

a. zinc acetate and
b. a combination of
   (b1) one or more of dibutyl tin oxide, stannous oxalate, zinc acetate, para-toluene sulphonic acid and phosphoric acid, and then
   (b2) an alkaline earth metal alkoxide

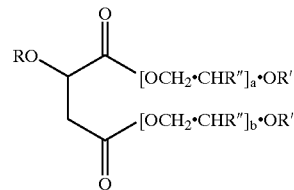

(I)

in which R'=R and R" is H or an alkyl or an alkylene group having 1 to 2 carbon atoms and, each of a and b is same or different and has a value of 0 or is an integer from 1–6.

By the expression "alkylene" as used herein and throughout the specification is meant a divalent hydrocarbyl group such as eg a —CH$_2$—(CHR")$_t$—CH$_2$— group wherein t=0 or an integer and R" has the same notation as above.

R' is derived from the reactant alcohol containing allylic unsaturation which can be modified by reaction with epoxides such as eg ethylene oxide and propylene oxide. Thus, R'O[CHR".CH$_2$O]$_x$H where x is 0 or an integer from 1–6 which is used for making the MOE and can be an allylic hydrocarbyl or an allylic hydrocarbyloxy alkylene group. Thus, the first reactant alcohol may be an allylic alcohol and includes inter alia 2-ethyl-hex-2-en-1-ol (which compound will hereafter be referred to as "2-ethylhexenol" for convenience); 2-octen-1-ol; 1-octen-3-ol; 2,7-octadienol; 2-ethyl allyl alcohol; hept-3-en-2-ol; 4-methyl pent-3-en-2-ol; 4-t-butoxy but-2-en-1-ol (also called 1,4-but-2-ene diol mono-tertiary butyl ether); 4-n-butoxy but-2-en-1-ol (also called 1,4-but-2-ene diol mono-n-butyl ether); cinnamyl alcohol; and isophorol.

The reactant R'O[CHR".CH$_2$O]$_x$H where x is 0 or an integer from 1–6 can be prepared in several ways known to those skilled in the art. For instance, the reactant alcohol, eg an allylic alcohol, used to produce the MOE of the present invention can be produced by the reduction of the corresponding α,β-unsaturated aldehyde eg by hydrogenation, which will generate a mixture of the allylic alcohol and its saturated analogue. Some other allylic alcohols may be produced from conjugated dienes via the well known addition reactions. Furthermore, other allylic alcohols may be produced by initially forming an unsaturated ester from an olefin and a carboxylic acid followed by hydrolysis of the ester to a mixture of isomeric allylic alcohols. This latter reaction may, like some of the other reactions mentioned above, result in a mixture of products which includes inter alia the desired allylic alcohol, isomers thereof and saturated analogues thereof. The mixtures of allylic alcohols with the saturated analogue thereof and/or the isomers thereof can be then used as such, or, after further purification to isolate the desired allylic alcohol, to prepare the MOE represented by formula (I) above.

Where the reactant alcohol is itself an allylic unsaturated hydroxy ether, ie x=1–6, this may be derived by alkoxylation of the alcohol, eg allylic unsaturated alcohol, suitably in the presence of a catalyst to form the hydroxy ether. Where a catalyst is used for this alkoxylation step, it should be such that it does not cause rearrangement of the allylic function and hence, amphoteric, basic or acidic catalysts may be used under mild conditions. The catalyst can be heterogeneous or homogeneous. The epoxidation step is suitably carried out in the presence of a base catalyst. Examples of base catalysts that may be used include alkali metal hydroxides such as sodium or potassium hydroxide and other metal salts such as potassium acetate.

The alkoxylation reaction to form the hydroxy ether of the allylic alcohol can be carried out using one or more of the epoxides which include inter alia ethylene oxide, propylene oxide, butene oxide and butadiene mono-oxide. The amount of epoxide used for this step would depend upon the number of alkoxy groups desired in the hydroxy ether. The amount of epoxide used is suitably in the range from 0.1 to 20 moles, preferably from 1 to 5 moles based on the allylic alcohol reactant.

The alkoxylation reaction is suitably carried out at a temperature in the range from 50 to 180° C., preferably from 60–140° C. The reaction pressure for this step is suitably autogenous but is preferably from 100 to 700 KPa.

The hydroxy ether formed in this step is suitably separated from the reaction mixture by neutralisation using eg magnesium silicate, then filtered to remove the neutralising agent and the salt of neutralisation so formed to leave behind a filtrate comprising the desired hydroxy ether.

The hydroxy ether so produced can be used either as such without purification, or, optionally, after purification (eg by distillation) for the esterification stage.

The MOE of formula (I) in the compositions according to the present invention can be prepared by a single-stage or two stage reaction. Where the single stage reaction is used, the dicarboxylic compound and the reactant alcohol R'O [CHR".CH$_2$O]$_x$H where x is 0 or an integer from 1–6, are reacted at a temperature in the range from 80–140° C. in the presence of the catalyst (a), ie zinc acetate. In this instance of the catalyst (a), the alcohol reactant is used in a molar excess, suitably using ratio of alcohol to dicarboxylic compound in the region of 2–4:1, preferably 2.5:1. Such a reaction is deemed to be complete when the level of half ester in the reaction mixture falls below about 0.5% w/w, preferably below 0.3% w/w. This can be monitored by analysing samples withdrawn from the reaction mixture. The reaction takes up to 8–10 hours for completion. The products from the reaction can be worked up by washing the reaction mixture initially with aqueous alkali and then with a brine solution until a steady pH is attained. This is then allowed to separate into an aqueous and an organic phase. The organic phase containing the desired MOE is then collected and heated in a rotary evaporator under reduced pressure to remove any remaining traces of water and any excess, unreacted alcohol reactant. The desired MOE left behind in the residual product can then be further purified by reduced pressure distillation at or below 100° C. and/or by treatment with eg activated carbon. The desired MOE can then be analysed by $13^C$ NMR, GC (a CP-SIL5 50 m capillary column and a flame ionisation detector) and by titrations to determine the structure and various other characteristics such as acid numbers, hydroxyl numbers and chemical composition.

Where the esterification is carried out using catalyst (b) it is suitably carried out in two stages. The first stage comprises reacting the reactant alcohol with maleic acid or anhydride and/or fumaric acid or esters thereof in the presence of catalyst component (b1). The catalyst component (b1) used in this step can be dibutyl tin oxide, stannous oxalate, zinc acetate, para-toluene sulphonic acid or phosphoric acid. This reaction is suitably carried out at a temperature below 150° C., preferably from 100–140° C. The completion of this first stage reaction is ascertained by GC analysis using a CP-SIL5 50 m capillary column and a flame ionisation detector.

Upon completion of the reaction, the unreacted materials are stripped out by steam stripping or by azeotropic distillation eg using an azeotroping agent such as eg cyclohexane. The catalyst may then be neutralised or removed as appropriate, the solids filtered and the MOE in the filtrate recovered.

The MOE from this initial step is then further reacted in a second step with the catalyst component (b2), an alkaline earth metal alkoxide, in the presence of a further aliquot of the reactant alcohol to enhance the 2-allyloxy succinate ester content thereof. The alkaline earth metal in the alkoxide is suitably magnesium. The reaction with the alcohol in the presence of the alkaline earth metal alkoxide is suitably carried out at a temperature below 120° C., suitably in the range from 40 to 80° C. and step (b) with catalyst (b2) is suitably carried out at atmospheric, subatmospheric or superatmospheric pressures. The pressures used are preferably in the range from atmospheric to 50 Kpa, more preferably from atmospheric to 5 KPa.

A feature of the two-stage process of the present invention is that it uses relatively milder conditions than a conventional Michael addition reaction. For instance, no reflux conditions need be used during this step. Furthermore, the present process enables the proportion of the 2-substituted succinate ester in the reaction product to be enhanced considerably without leading to undesirable polymer formation or increasing the colouration of the ester product. Moreover, the present process not only gives better yields of the desired 2-substituted succinate ester.

The MOE of the present invention have low volatility and relatively low viscosity suitably below 1500 mPa.s, thereby rendering them a suitable solvent component for curable paint and varnish formulations. These MOEs are especially suitable a the so called "reactive dilutents" for paint formulations and in particular those containing alkyd resins. Reactive diluents are usually compounds or mixtures of compounds of relatively low viscosity, a relatively high boiling point (or low saturated vapour pressure) which act as solvents during the formulation and processing of the coating. An advantage of reactive diluents is that such diluents can copolymerise with components of the alkyd resin. Hence reactive diluents may be used to replace part or all of the traditional solvents normally used in such formulations thereby reducing losses of the solvent to atmosphere on drying of the coating. Use of reactive diluents comprising esters of polyhydric alcohols which have been partially etherified with allyl alcohol are described in EP-A-0 253 474.

Alkyd resins are well known components of decorative paints (see, for example, "The Technology of Paints, Varnishes and Lacquers" by C R Martens (Ed.), published by Robert Krieger Publishing (1974) and can be prepared from polybasic acids or anhydrides, polyhydric alcohols and fatty acids or oils. U.S. Pat. No. 3,819,720 describes methods of preparing such alkyd formulations. Alkyd coating compositions usually contain large amounts of solvents (eg mineral spirits and aromatic hydrocarbons).

The compositions of the present invention are highly suitable for use as reactive diluents. The relative ratios of reactive diluent to the alkyd resin in a formulation can be derived from the ranges quoted in published EP-A-0 305 006. In an example in which the reactive diluent replaces all of the traditional solvent, the ratio of reactive diluent to alkyd resin is suitably in the range from 1–50:99–50 parts by weight, eg 5–50:95–50 parts by weight, preferably from 5–25:95–75 and more preferably from 5–15:95–85 parts by weight. On the other hand, where used in a conventional paint formulation, such a diluent can replace all or part of a traditional solvent such as white spirit. The formulations may contain further components such as catalyst, drier, antiskinning agent, pigments, pigment stabilisers, rheology controllers (e.g. for sag control), UV and oxidation stabilisers, flow additives, microgels (e.g. to enhance hardness) and other additives. The formulations may also need to include water scavengers such as trialkyl orthoformates, molecular sieves or zeolites where the reactive diluent used is susceptible to hydrolysis such as eg some of the ether ester derivatives. Furthermore, where such water scavengers are used it may be necessary to use them in combination with compatible pigment stabilizers. Where a drier (siccative) is used this may further contribute towards the solvent content of the formulation.

For formulations comprising an oxidatively curing alkyd resin and a siccative/drier such as cobalt complexes, impurities which can have a co-ordination affinity for the siccative drier such as cobalt complexes can affect adversely the drying speed and stability of the paint. Examples of such impurities include maleic acid and triethyl amine. In particular, it has been found desirable to minimise the acidity of the ester mixture used as reactive diluent in such formulations to a value of <7000 ppm, preferably <3000 ppm, more preferably <1000 ppm w/w of KOH.

It has also been found that when MOEs, ie the succinates, fumarates and maleates, is used as a reactive diluent in such formulations comprising an oxidatively curing alkyd resins, the properties/performance of the diluent can be varied by changing the relative proportions of the three esters present in such a diluent. For example, mixtures with a relatively lower amount of maleates exhibit better hardness and drying properties compared with those having relatively higher amounts of such maleates. Moreover, it has also been observed that formulations comprising these MOEs display a decreased tendency towards wrinkling. This renders them particularly suitable when using formulations comprising high solid systems/one-coat paints have to be applied to generate a greater thickness of the relevant coating without impairing the ability of such thicker layers to harden through.

For some uses it is preferable that the free alcohol content of the diluent is minimised in order to facilitate drying of the formulation.

A feature of the present invention is that ether esters of formula (I) when used as reactive diluents in paint or coating formulations, especially those comprising alkyd resins, enhance the performance of these formulations. In particular, where a mixture of products comprising ether esters of the present invention derived by reacting an allylic alcohol or a hydroxy ether thereof with maleic acid/anhydride or fumaric acid is used as reactive diluent, they enhance their performance when compared with that of the unsaturated esters when used alone.

A further aspect of the present invention is that such esters when used in a relatively pure state do not cause any haze in the formulation. Where there is likely to be a risk of such haze formation, eg due to the presence of impurities such as eg resins or polymers formed during the synthesis of the esters used or during storage of such formulations, it is beneficial to use inhibitors such as eg butylated hydroxytoluene (2,6-butoxy-4-methyl phenol) or 2,4,6-tert-butyl phenol. Such inhibitors not only have the advantage of preventing haze formation but also render the formulations safer to handle by inhibition of other unwanted reactions in the formulation such as eg peroxidation.

Uses of the molecules of this invention include the partial or total replacement of traditional hydrocarbon-based solvents in solvent-borne alkyd paints used for primer, undercoat and topcoat decorative applications as well as in industrial applications such as alkyd primers and UV-cure.

The molecules of this invention are also suitable for use as co-monomers, for example in vinyl acetate-based polymers used in emulsion paints. In this case, the molecules of this invention impart a temporary plasticisation to the paint film, before air-curing to a hard finish. They can, therefore, facilitate the partial or total replacement of coalescent solvents.

In addition, the molecules could be used in water-based paints based on acrylic and alkyd resins, in addition to, or instead of, coalescent solvents.

The present invention is further illustrated with reference to the following Examples.

EXAMPLES

1. Examples of the Preparation of the Reactive Diluents

Example S1

The following apparatus was assembled: A five-liter flanged flask with an insert pipe for a nitrogen sparge, a thermowell for thermocouple, and a Dean and Stark apparatus with double-walled condenser. The flask was heated with an electric heating mantle which was controlled with a eurotherm controller connected to the thermocouple. The nitrogen sparge pipe was inserted so that the nitrogen flow agitated the flask contents and provided mixing during the course of the reaction. The nitrogen flow also served to entrain out the liberated methanol and force the reaction to completion.

To the flask was added dimethyl maleate (867.2 g), 2,7-octadienol (2301 g) and zinc acetate (31.44 g). The mixture was sparged with nitrogen for 10 minutes to remove air and the nitrogen flow was then reduced to a level which ensured efficient mixing. The mixture was then heated in stages to 130° C. (ie 80° C. for 10 minutes, then 100° C. for 10 minutes and then 120° for 10 minutes). The progress of the reaction was monitored by the methanol collected in the Dean and Stark apparatus. When 90% of the predicted methanol had been collected, the reaction mixture was sampled hourly and analysed by GC. The reaction was adjudged complete when the level of the "half ester" (methyl octadienyl maleate/fumarate) fell to below 0.3% w/w, this took approximately 8 hours. At this point the heating was switched off and the reaction mixture allowed to cool to room temperature. The product from the reaction was then decanted from any solids in the reaction flask. This product was then charged to a heated decanter (40° C.) with an equal volume of 5% w/w aqueous sodium hydroxide solution. The mixture was stirred for 20 minutes and then allowed to separate and the lower aqueous phase decanted. The base wash was then repeated and the remaining organic phase was washed with saturated brine until the aqueous phase reached a steady pH. The organic phase was then heated (100° C.) under reduced pressure (<500 Pa(<5 mBar)) on a rotatory evaporator to remove residual water and the majority of the excess octadienol. After cooling, the product was filtered and transferred to a 5-liter three necked round bottomed quickfit flask. This flask was equipped with a still head condenser and receiver flask (Perkin triangle), a thermocouple, a steam inlet pipe, and a eurotherm controlled heating mantle. The apparatus was evacuated to 4000 Pa (40 mBar) and the product heated to 120° C. The supply of steam was then connected and the residual traces of octadienol were removed. The purification was judged complete when the volume of the heads product aqueous phase increased to more than 5 times that of the organic phase. After cooling down, the product was then treated with activated carbon (1%w/w, 100° C. 2 Hrs, <500 Pa(<5 mBar)) on a rotatory evaporator. The cooled mixture was filtered through dried celite to obtain the final product which had the following analyses:

| | |
|---|---|
| OH number | 7 mg KOH/g (titration) |
| total acid | 226 ppm KOH/g (titration) |
| maleic acid/anhydride | <10 ppm (HPLC) |
| Fumaric acid | <10 ppm (HPLC) |
| Zinc | <5 ppm (atomic absorption, detection limit) |
| sodium | 30 ppm (atomic absorption) |
| chlorine | <10 ppm (atomic absorption detection limit) |
| GC "CPSil5" column | 2,7-octadienyl methyl fumarate/maleate (0.1% w/w) |
| | di-(2,7-octadienyl) maleate (11% w/w) |
| | di-(2,7-octadienyl) fumarate (43% w/w) |
| | 2-(2,7-octadienoxy) di-(2,7-octadienyl) succinate (41% w/w) |
| | higher boilers (0.01% w/w) |

The GC assignment was supported by GC/MS and a $^1$H nmr and $^{13}$C nmr studies. The GC/MS used a VG Trio-1000, operated according to the manufacturers instructions under the following conditions:

GC column 25 m×0.32 mm DB5 (0.25 micron film)

temperature programme 40° C. (3 mins) @10° C./min to 320° C. (10 mins).

injection 1 microliter (1% solution in acetone) on column 40° C.

ammonia chemical ionisation (CI)

scan range 50–800 scan rate 1/s

It was found that the deduction of molecular weights from the CI spectra is rather less straightforward than is usual on account of (a) extensive rearrangements of fumarates in particular giving [M+3]+ and [M+20]+ ions in addition to the usual [M+1]+ and [M+18] ions and (b) extensive fragmentation exhibited by some species. As a result, the GC peaks have been assigned by interpretation. These assignments were confirmed by $^1$H and $^{13}$C nmr. Table 1 gives assignments of the observed $^{13}$C nmr peaks. It should be noted that the two isomeric octadienols (2,7-octadienol and 1,7-octadien-3-ol) though not separable by the GC method used can nevertheless be identified by nmr and are recorded in the nmr assignment Table 1. The correspondence to the GC was again confirmed by integration of the nmr spectrum of several samples in which the composition varied. The product of this reaction will hereafter be called sample AK1.

Comparative Example S2

The following apparatus was assembled: A five-liter flanged flask with an insert pipe for a nitrogen sparge, a thermowell for thermocouple, and a Dean and Stark apparatus with double-walled condenser. The flask was heated with an electric heating mantle which was controlled with a eurotherm controller connected to the thermocouple. The nitrogen sparge pipe was inserted so that the nitrogen flow agitated the flask contents and provided mixing during the course of the reaction. The nitrogen flow also served to entrain out the liberated methanol and force the reaction to completion.

To the flask was added dimethyl maleate (1004.1 g), 2,7-octadienol (2620.2 g) and stannous oxalate (36.5 g). The mixture was sparged with nitrogen for 10 minutes to remove air and the nitrogen flow was then reduced to a level which ensured efficient mixing. The mixture was then heated in stages to 130° C. (e.g. 80° C. for 10 minutes, then 100° C. for 10 minutes and then 120° C. for 10 minutes). The progress of the reaction was monitored by the methanol collected in the Dean and Stark apparatus. In order to drive the reaction to completion the temperature was raised to 140° C. after 40 hrs at 130° C. When 90% of the predicted methanol had been collected, the reaction mixture was sampled hourly and analysed by GC. The reaction was adjudged complete, when the level of the "half ester" (methyl octadienyl maleate/fumarate) fell to below 0.3% w/w and this took approximately 72 hours. At this point the heating was switched off and the reaction mixture allowed to cool to room temperature. The product from the reaction was then decanted from any solids in the reaction flask. This product was then charged to a heated decanter (40° C.) with an equal volume of 5% w/w aqueous sodium hydroxide solution. The mixture was stirred for 20 minutes and then allowed to separate and the lower aqueous phase decanted. This base wash was then repeated and the remaining organic phase was washed with saturated brine until the aqueous phase reached a steady pH. The organic phase was then heated (100° C.) under reduced pressure (<500 Pa(<5 mBar)) on a rotatory evaporator to remove residual water and the majority of the excess octadienol. After cooling, the product was filtered and transferred to a 5-liter three-necked round-bottomed quickfit flask. This flask was equipped with a still head condenser and receiver flask (Perkin triangle), a thermocouple, a steam inlet pipe, and a eurotherm controlled heating mantle. The apparatus was evacuated to 4000 Pa (40 mBar) and the product heated to 120° C. The supply of steam was then connected and the residual traces of octadienol were removed. The purification was judged complete when the volume of the heads product aqueous phase increased more than 5 times that of the organic phase. After cooling down, the product was then treated with activated carbon (1% w/w, 100° C. 2 hrs, <500 Pa(<5 mBar)) on a rotatory evaporator. The cooled mixture was filtered through dried celite to obtain the final product which had the following analyses:

| | |
|---|---|
| OH number | 1 mg KOH/g (titration) |
| total acid | 113 ppm KOH/g (titration) |
| maleic acid/anhydride | <10 ppm (HPLC) |
| Fumaric acid | <10 ppm (HPLC) |
| tin | <5 ppm (atomic absorption, detection limit) |
| sodium | <20 ppm (atomic absorption, detection limit) |
| chlorine | <10 ppm (atomic absorption detection limit) |
| GC "CPSil5" column | 2,7-octadienyl methyl fumarate/maleate (1.1% w/w) |
| | di-(2,7-octadienyl) maleate (69% w/w) |
| | di-(2,7octadienyl) fumarate (22% w/w) |
| | 2-(2,7-octadienoxy) di-(2,7-octadienyl) succinate (5% w/w) |

The GC assignment was supported by GC/MS and a $^1$H nmr and $^{13}$C nmr studies. The GC/MS used a VG Trio-1000, operated according to the manufacturers instructions under the following conditions:

GC column 25 m×0.32 mm DB5 (0.25 micron film)

temperature programme 40° C. (3 mins) @10° C./min to 320° C. (10 mins)

injection 1 microliter (1% solution in acetone) on column 40° C.

ammonia chemical ionisation (CI)

scan range 50–800 scan rate 1/s

It was found that the deduction of molecular weights from the CI spectra is rather less straightforward than is usual on account of (a) extensive rearrangements of fumarates in particular giving [M+3]+ and [M+20]+ ions in addition to the usual [M+1]+ and [M+18] ions and (b) extensive fragmentation exhibited by some species. As a result the GC peaks were assigned by interpretation. In addition to the assigned peaks an additional species was identified which was assigned to a lactone.

This assignment was confirmed by $^1$H and $^{13}$C nmr. Table 1 gives assignments of the observed $^{13}$C nmr peaks. It should be noted that the two isomeric octadienols (2,7-octadienol and 1,7-octadien-3-ol) though not separable by the GC method used can be identified by nmr and are recorded in the nmr assignment Table 1. The correspondence to the GC was confirmed by integration and analysis of several samples in which the composition varied. The lactone found by GC/MS was also observed in the nmr and quantified at approximately 7.1% (tenative structure given in Table 1). The product of this Example will hereafter be called sample AK2.

Comparative Example S3

The following apparatus was assembled: A five-liter flanged flask with an insert pipe for a nitrogen sparge, a thermowell for thermocouple, and a Dean and Stark apparatus with double-walled condenser. The flask was heated with an electric heating mantle which was controlled with a eurotherm controller connected to the thermocouple. The nitrogen sparge pipe was inserted so that the nitrogen flow agitated the flask contents and provided mixing during the course of the reaction. The nitrogen flow also served to entrain out the liberated methanol and force the reaction to completion.

To the flask was added dimethyl maleate (914.3 g), 2,7-octadienol (2375 g) and stannous oxalate (31.2 g). The mixture was sparged with nitrogen for 10 minutes to remove air and the nitrogen flow was then reduced to a level which ensured efficient mixing. The mixture was then heated in stages to 130° C. (e.g. 80° C. for 10 minutes, then 100° C. for 10 minutes and then 120° C. for 10 minutes). The progress of the reaction was monitored by collection of the methanol collected in the Dean and Stark apparatus. In order to drive the reaction to completion the temperature was raised to 140° C. after 7 hrs at 130° C. When 90% of the methanol had been collected, the reaction mixture was sampled hourly and analysed by GC. The reaction was adjudged complete when the level of the "half ester" (methyl octadienyl maleate/fumarate) fell to below 0.3% w/w and this took approximately 31 hours. At this point the heating was switched off and the reaction mixture allowed to cool to room temperature. The product from the reaction was then decanted from any solids in the reaction flask. This product was then charged to a heated decanter (40° C.) with an equal volume of 5% w/w aqueous sodium hydroxide solution. The mixture was stirred for 20 minutes and then allowed to separate and the lower aqueous phase decanted. This base wash was repeated and the remaining organic phase was washed with saturated brine until the aqueous phase reached a steady pH. The organic phase was then heated (100° C.) under reduced pressure (<500 Pa(<5 mBar)) on a rotatory evaporator to remove residual water and the majority of the excess octadienol. After cooling, the product was filtered and transferred to a 5-liter three-necked round-bottomed quickfit flask. This flask was equipped with a still-head condenser and receiver flask (Perkin triangle), a thermocouple, a steam inlet pipe, and a eurotherm controlled heating mantle. The apparatus was evacuated to 4000 Pa (40 mBar) and the product heated to 120° C. The supply of steam was then connected and the residual traces of octadienol were removed. The purification was judged complete when the volume of the heads product aqueous phase increased more than 5 times that of the organic phase. After cooling down the product was then treated with activated carbon (1%w/w, 100° C. 2 hrs, <500 Pa(<5 mBar)) on a rotatory evaporator. The cooled mixture was filtered through dried celite to obtain the final product which had the following analyses:

| | |
|---|---|
| OH number | 4 mg KOH/g (titration) |
| total acid | 46 ppm KOH/g (titration) |
| maleic acid/anhydride | <10 ppm (HPLC) |
| Fumaric acid | <10 ppm (HPLC) |
| tin | <10 ppm (atomic absorption) |
| sodium | <20 ppm (atomic absorption, detection limit) |
| chlorine | <10 ppm (atomic absorption detection limit) |
| GC "CPSil5" column | octadienyl methyl fumarate/maleate (0.11% w/w) |
| | di-(2,7-octadienyl) maleate (73% w/w) |
| | di-(2,7-octadienyl) fumarate (22% w/w) |
| | 2-(2,7-octadienoxy) di-(2,7-octadienyl) succinate (3% w/w) |

The GC assignment was supported by GC/MS and a $^1$H nmr and $^{13}$C nmr studies. The GC/MS used a VG Trio-1000, operated according to the manufacturers instructions under the following conditions:

GC column 25 m×0.32 mm DB5 (0.25 micron film)

temperature programme 40° C. (3 mins) @10° C./min 320° C. (10 mins)

injection 1 microliter (1% solution in acetone) on column 40° C.

ammonia chemical ionisation (CI)

scan range 50–800 scan rate 1/s

It was found that the deduction of molecular weights from the CI spectra is rather less straightforward than is usual on account of (a) extensive rearrangements of fumarates in particular giving [M+3]+ and [M+20]+ ions in addition to the usual [M+1]+ and [M+18] ions and (b) extensive fragmentation exhibited by some species. As a result the GC peaks were assigned by interpretation. In addition to the assigned peaks an additional species was identified which was assigned to a lactone. This assignment was confirmed by $^1$H and $^{13}$C nmr. Table 1 gives assignments of the observed $^{13}$C nmr peaks. It should be noted that the two isomeric octadienols (2,7-octadienol and 1,7-octadien-3-ol) though not separable by the GC method used can be identified by nmr and are recorded in the nmr assignment Table 1. The correspondence to the GC was confirmed again by integration of the nmr spectrum of several samples in which the composition varied. The lactone found by GC/MS was also observed in the nmr and quantified at approximately 6.2% (tenative structure given in Table 1). The sample is hereafter referred to as AK2R.

Example S4

The process of Example S1 was repeated to give a product with the following analysis:

| | |
|---|---|
| OH number | <1 mg KOH/g (titration) |
| total acid | 91 ppm KOH/g (titration) |
| maleic acid/anhydride | <10 ppm (HPLC) |
| Fumaric acid | <10 ppm (HPLC) |
| Zinc | <5 ppm (atomic absorption, detection limit) |
| sodium | <20 ppm (atomic absorption) |

-continued

| | |
|---|---|
| chlorine | <10 ppm (atomic absorption detection limit) |
| GC "CPSil5" column | 27-octadienyl methyl fumarate/maleate (0.02% w/w) |
| | di-(2,7-octadienyl) maleate (1.4% w/w) |
| | di-(2,7-octadienyl) fumarate (55% w/w) |
| | 2-(2,7-octadienoxy) di-(2,7-octadienyl) succinate (42% w/w) |
| | higher boilers (<0.01% w/w) |

The GC assignment was supported by GC/MS and a $^1$Hnmr and $^{13}$C nmr studies.

The sample from this example is hereafter referred to as AK1R.

Comparative Example S5

The following apparatus was assembled: A one-liter flanged flask with an insert pipe for a nitrogen sparge, a thermowell for thermocouple, a magnetic follower, and a double-walled condenser. The flask was heated with an electric heating mantle which was controlled with a eurotherm controller connected to the thermocouple. The nitrogen sparge pipe was inserted so that the flask and contents could be purged of air prior to the reaction and the pipe raised to provide a top cover during the course of the reaction, the reactor contents were stirred with the polytetrafluoroethylene coated magnetic follower. To the flask was added AK2R (500 g), 2,7-octadienol (1.5 molar equivalents) and sufficient magnesium ethoxide to neutralise the residual acidity as measured by the total acid number analysis (it was assumed that 1 mole of magnesium ethoxide neutralised one mole of acid). To this mixture was then added a further 0.35% w/w magnesium ethoxide based on the total reaction mixture weight. The magnetic stirrer was then switched on and the mixture sparged with nitrogen for 10 minutes to remove air and the nitrogen flow was then redirected to provide a nitrogen top cover. The mixture was heated to 60° C. The progress of the reaction was monitored by GC analysis. The reaction was judged complete after 16 Hrs. The heating was switched off and the mixture allowed to cool. The mixture was then washed repeatedly with an equla volume of de-ionised water t, at room temperature for 20 minutes, to remove the magnesium catalyst. This was judged complete when the pH of the lower aqueous phase remained steady. This took three washes. The organic phase was then heated (100° C.) under reduced pressure (<500 Pa(<5 mBar)) on a rotatory evaporator to remove residual water and the majority of the excess octadienol. After cooling, the product was filtered and transferred to 1-liter three-necked round-bottomed quickfit flask. This flask was equipped with a still head condenser and receiver flask (Perkin triangle), a thermocouple, a steam inlet pipe, and a eurotherm controlled heating mantle. The apparatus was evacuated to 4000 Pa (40 mBar) and the product heated to 120° C. The supply of steam was then connected and the residual traces of octadienol were removed. The purification was judged complete when the volume of the heads product aqueous phase increased more than 5 times that of the organic phase. After cooling down, the product was then treated twice with activated carbon (1% w/w, 100° C. 2 Hrs, <500 Pa(<5 mBar)) on a rotatory evaporator. After each treatment the cooled mixture was filtered through dried celite to remove the activated carbon. The final product contained by GC 97% 2-(2,7-octadienoxy)di-(2,7-octadienyl)succinate with the remainder being composed of traces of residual octadienol, mixed methyl 2,7-octadienyl maleates/fumarates and di-(2,7-octadienyl)maleate/fumarate. This sample is thereafter refered to as AK2S.

TABLE 1

2.7-Octadienol: $CH_2$=$CH \cdot CH_2 \cdot CH_2 \cdot CH_2 \cdot CH$=$CH \cdot CH_2 \cdot OH$ (positions 8 7 6 5 4 3 2 1)

| | 1 | 2 | 3 | 4 | 5 | 6 | 7 | 8 |
|---|---|---|---|---|---|---|---|---|
| Major | 63 | 132.8 | 129.5 | 31.3 | 28.6 | 33 | 138.5 | 114.5 |
| Minor | 58 | 132 | 129 | 26.6 | 28 | 33 | 135.5 | 114.5 |

Fumarate/Maleate: $CH_2$=$CH \cdot CH_2 \cdot CH_2 \cdot CH_2 \cdot CH$=$CH \cdot CH_2 \cdot O \cdot (C$=$O)C \cdot C$=$C \cdot C(C$=$O) \cdot OR$ (R = 2,7-Octadienol) (positions 8 7 6 5 4 3 2 1 9 10)

| Fumarate/Maleate | 1 | 2 | 3 | 4 | 5 | 6 | 7 | 8 | 9 | 10 |
|---|---|---|---|---|---|---|---|---|---|---|
| Maleate (major isomer) | 65.24 | 123.34 | 135.81 | 31.12 | 27.53 | 32.65 | 137.8 | 114.3 | 164.27 | 129.33 |
| Maleate (minor isomer)* | 60.4 | — | — | 26.39 | 28.04 | 32.65 | — | — | 164.42 | 129.39 |
| Fumarate (major isomer) | 65.35 | 123.31 | 136.16 | 31.2 | 27.58 | 32.73 | 137.81 | 114.42 | 163.96 | 133.12 |
| Fumarate (minor isomer)* | 68.72 | 122.83 | 135.02 | 26.49 | 28.1 | 32.79 | 137.81 | 114.51 | 164.07 | 133.21 |

*Some of the assignments are tentative 2-(2,7-octadienoxy)di-2,7-octadienyl succinate $CH_2$=$CH \cdot CH_2 \cdot CH_2 \cdot CH_2 \cdot CH$=$CH \cdot CH_2 \cdot O \cdot (O$=$)C \cdot CH_2 \cdot CH \cdot (C$=$O) \cdot O$ (positions 8 7 6 5 4 3 2 1 9 10 11 12)

$CH_2 \cdot CH$=$CH \cdot CH_2 \cdot CH_2 \cdot CH_2 \cdot CH$=$CH_2) \cdot O \cdot CH_2 \cdot CH$=$CH \cdot CH_2 \cdot CH_2 \cdot CH_2 \cdot CH$=$CH_2$ (positions 1' < 2' - 8' > 1" 2" 3" 4" 6 5" 7" 8")

| | 1 | 2 | 3 | 4, 4', 4" | 5, 5' | 6, 6', 6" | 7, 7' | 8, 8' | 9 | 10 | 11 | 12 |
|---|---|---|---|---|---|---|---|---|---|---|---|---|
| Major | 65.15 | 123.52 | 135.9 | 31.2 | 27.58 | 32.73 | 137.81 | 114.51 | 169.18 | 37.53 | 73.51 | 170.69 |
| Minor | 60.31 | — | — | 26.49 | 28.1 | 32.79 | — | — | 169.27 | — | 73.7 | 170.78 |

TABLE 1-continued

| | 1' | 2' | 3' | 1" | 2" | 3" | 5" | 7" | 8" |
|---|---|---|---|---|---|---|---|---|---|
| Major | 64.94 | 123.75 | 135.38 | 71.24 | 125.66 | 134.55 | 27.76 | 137.96 | 114.2 |
| Minor | 60.13 | — | — | 65.89 | — | — | — | — | — |

Lactones: Species believed to be lactones have been identified in the octadienyl ester samples. Whilst there appear to be two possible isomers of this lactone, the 13C NMR data fits the following structure:

$$\underset{8\quad\quad 7\ \ 6\ \ 5\ \ 4\quad\ \ 3\ \ 2\ 11\ 10\ \ 9\quad\quad\quad 1'}{CH_2\!=\!CH\cdot CH_2\cdot CH_2\cdot CH\!=\!CH\cdot CH\cdot CH\cdot CH_2\cdot C(\!=\!O)\cdot O\cdot CH_2\cdot CH\!=\!CH\cdot CH_2\cdot CH_2\cdot CH_2\cdot CH\!=\!CH_2}$$

with lactone ring: $_1CH_2\!-\!O\!-\!_{12}C(\!=\!O)$

| | 11' | 2 | 3 | 9 | 10 | 11 | 12 | 1' |
|---|---|---|---|---|---|---|---|---|
| Isomer 1 | 71.28 | 41.47 | 125.33 | 170.49 | 30.45 | 39.47 | 176.43 | 64.94 |
| Isomer 2 | 69.81 | 45.00 | 126.58 | 170.01 | 31.69 | 41.59 | 176.30 | 64.96 |

2. Viscosity Measurements of the Reactive Diluents 2.1 Method

The viscosity of each diluent was measured at 25° C. using a suspended level viscometer. Densities of the diluents were taken as an average of three readings made at 25° C. using density bottles with a nominal 10 cm3 capacity, calibrated with water.

2.2 Results

TABLE 2

Viscosity of reactive diluents

| Diluent | Viscosity (m Pa · s) |
|---|---|
| AK1 (Example S1) | 59 |
| AK2 (Example S2) | 19 |
| AK2R (Example S3) | 18 |
| AK1R (Example S4) | 51 |
| AK2S (Example S5) | 21 |

Table 2 demonstrates that the esters/reactive diluents of this invention have relatively low viscosity (<200 mPa.s) and are suitable for use as reactive diluents.

3. Examples of the Use of the Reactive Diluents in Paint Formulations

Reactive diluents, such as those of the present invention, must meet a range of criteria including low odour and low toxicity, low viscosity and the ability to "cut" the viscosity of the paint to facilitate application on the surface to be coated therewith. Furthermore, the diluent should not have a markedly adverse effect on the properties of the paint film such as drying speed, hardness and degree of wrinkling. The reactive diluents described above have therefore been tested in paint applications using both clear and pigmented paints. The diluents have been compared with paints formulated using white spirit, a conventional thinner. The results demonstrate the excellent performance of the diluents of this invention.

3.1 Tests of Pigmented Paint Formulations

NB. It is well known by those skilled in the art that day-to-day fluctuations in conditions can introduce some variability into experimental data. To minimise these errors, the tests presented below were conducted as follows: ca. five to ten paint formulations were prepared simultaneously and comprised one reference (white spirit) and about four to nine reactive diluent-based paints. These samples were tested at the same time under identical conditions. Comparison of performance data from within these groups of formulations allowed errors due to random sources to be minimised.

Hence, in the following examples the reader will realise that the apparent variation in performance data from some diluents results from the use of different paint formulations made on different days from the same diluent.

a) Methods Used to Prepare Paint Formulations

NB. In the examples below, % reactive diluent refers to the ratio of reactive diluent to alkyd (e.g. 30% reactive diluent implies 30 g diluent to every 70 g alkyd).

i) Pigmented Paint Formulations Based on a High Solids Alkyd Resin

High Solids Alkyd Reference with White Spirit Diluent

In a mini motor mill 534 grams of a high solids alkyd (Setal® 293, ex. Akzo Nobel Resins) and 423 grams of titanium dioxide (Kronos® 2310, ex. Kronos) were milled. Thereafter 40 grams of a combi siccative (Nuodex Combi® APB, ex. Servo) and 2.9 grams of methyl ethyl ketoxime were added and mixed thoroughly. This mixture was diluted with white spirit to an application viscosity of 0.5 Pa.s.

High Solids Alkyd with 30% of Reactive Diluent

In a mini motor mill 374 grams of a high solids alkyd (Setal® 293, ex. Akzo Nobel Resins) and 423 grams of titanium dioxide (Kronos® 2310, ex. Kronos) were milled. Thereafter 160 grams of 'AK1', 40 grams of a "combi siccative" (Nuodex Combia APB, ex. Servo) and 2.9 grams of methyl ethyl ketoxime were added and mixed thoroughly. This mixture was diluted with white spirit to an application viscosity of 0.5 Pa.s.

A similar method (with appropriate adjustments to the proportions of the components of the paint) was used to prepare paints with 10 and 20% reactive diluent.

ii) Pigmented Paint Formulations Based on a Conventional Alkyd Resin

Conventional Alkyd Reference with White Spirit Diluent

In a mini motor mill 563 grams of a conventional alkyd (Setal® 270WS70, ex. Akzo Nobel Resins) and 306 grams of titanium dioxide (Tioxide® TR92, ex. Tioxide) were milled. Thereafter 2.4 grams of Siccatol® Co (10%) (ex. Durham Chemicals), 8.5 grams of Siccatol® Sr (10%) (ex. Durham Chemicals), 11.5 grams of Siccatol® Ca (5%) (ex. Durham Chemicals) and 3.0 grams of methyl ethyl ketoxime were added and mixed thoroughly. This mixture was diluted with white spirit to an application viscosity of 0.5 Pa.s.

Conventional Alkyd with 20% of Reactive Diluent

In a mini motor mill 448 grams of a conventional alkyd (Setal® 270WS70, ex. Akzo Nobel Resins) and 306 grams of titanium dioxide (Tioxide® TR92, ex. Tioxide) were milled. Thereafter 80 grams of 'AK-1', 2.4 grams of Siccatol® Co (10%) (ex. Durham Chemicals), 8.5 grams of Siccatol® Sr (10%) (ex. Durham Chemicals), 11.5 grams of Siccatol® Ca (5%) (ex. Durham Chemicals) and 3.0 grams of methyl ethyl ketoxime were added and mixed thoroughly. This mixture was diluted with white spirit to an application viscosity of 0.5 Pa.s.

Each of the pigmented paints prepared as described above was stored in two tins. One tin was kept at 23° C. for 7 days before testing. The second tin was stored at 35° C. for 2 weeks before drying speed tests were performed. The results below derive from the tins stored at 23° C. unless stated.

b) Test Methods Used with Pigmented Paint Formulations

Coating viscosity was measured in accordance with the ICI Cone & Plate method (ISO2884) at 10,000 s-1, 23° C., 50% RH (Pa.s).

König hardness (ISO1522) was measured at 23° C., 50% RH (s) of a coating film applied with a 100 mm applicator on a glass substrate.

The Fischer spherical indention test is based on ISO6441 (um) and was performed on a coating film applied with a 100 mm applicator on a glass substrate.

Drying performance was determined at 10° C., 85% RH with a Beck-Koller drying recorder (hours) under daylight lamps. Films were applied to glass substrates using a 90 mm applicator. The measurements quoted (in hours) are:

a) For high solids alkyd resin-based pigmented paints: "phase 1", the dust drying time;

b) For conventional alkyd resin-based pigmented paints: "phase 2" (touch dry time) and "phase 3" (through-dry time).

c) Results of the tests of pigmented paints based on reactive diluents i) Pigmented Paints Based on the High Solids Alkyd Example T1

Paints containing 30% reactive diluent were prepared from the diluents AK1, AK2, AK2R The drying speed results in Table 3 show that paints based on the reactive diluents of this invention dry over a period which is acceptable to the industry. Moreover, it is notable that the paints based on diluents with the composition of this invention show faster drying after storage at 35 C for two weeks than the paints based on the diluents in comparative examples AK2 and AK2R.

The Fischer indentation test and König hardness test results in Table 4 show that paint films containing the reactive diluents of this invention are relatively hard. This is a considerable advantage since many so-called reactive diluents cause plasticisation of the paint film. In contrast, the results in Table 4 are evidence that the diluents of this invention are bound into the paint film. Moreover, it is notable that the diluents with the composition of this invention give paints which show greater hardness than do the comparative examples AK2 and AK2R.

TABLE 3

(Drying performance)

| Diluent Used | Drying time (hours) of paint stored for 1 Week at 23° C. | Increase in drying time (hours) of paint stored for 2 weeks at 35° C. |
|---|---|---|
| Ester Mix Example S1 (AK1) | 6.5 | 2.5 |
| Ester Mix Example S2 (AK2)* | 7 | 5.75 |
| Ester Mix Example S3 (AK2R)* | 7.5 | 4.75 |

TABLE 4

(Hardness Data)

| Reactive Diluent Used | Indentation (microns) | | König hardness ** | |
|---|---|---|---|---|
| Ester Mix AK1 | 1.61* | 0.96# | 16@ | 23# |
| Ester Mix AK2 | 2.07* | 1.30# | 12@ | 18# |
| Ester Mix AK2R | 2.08* | 1.26# | 12@ | 18# |

*Film cured for 1 week at 23° C.
After 100 hours at 50° C.
@After 3 weeks at 23° C.
** In number of swings. Multiply by 1.4 to convert to seconds.

The results in Table 5 show the maximum thickness of paint which can be applied to a glass substrate without the appearance of unsightly wrinkles in the dried film. The reactive diluents of this invention allow relatively thick films to be applied—this is a considerable advantage for high solids and "one-coat" paints. The data in the table also show that very high solids contents can be achieved with the reactive diluents of this invention.

TABLE 5

| Diluent | Maximum film thickness* | Solids content ** |
|---|---|---|
| AK1 | 300 | 94 |
| AK2 | 300 | 97 |
| AK2R | 300 | 97 |

*Expressed as bar coater gap width (microns)
** Solids content of paint in weight %

Example T2

Further paint formulations were prepared using the high solids resin with different concentrations of diluent (expressed as % cf. the resin, i.e. 10% means 10% diluent to 90% resin). Table 6 shows the hardness data from these samples, again demonstrating that films with very good hardness can be obtained by using the diluents of this invention.

TABLE 6

(Hardness Data)

| Diluent Used | Indentation (microns) | | König hardness (**) | |
|---|---|---|---|---|
| AK1 (10%) | 1.37* | 1.07# | 14@ | 18# |
| AK1 (20%) | 1.24* | 0.82# | 16@ | 24# |
| AK1 (30%) | 1.19* | 0.66# | 20@ | 32# |
| White spirit | 1.29* | 1.1# | 13@ | 16# |

*After 1 week curing at 23° C.
After 100 hours at 50° C.
@After 3 weeks at 23° C.
** In number of swings. Multiply by 1.4 to convert to seconds.

ii) Pigmented Paints Based on the Conventional Alkyd

It is possible to use the reactive diluents of the present invention in paints, based on a wide range of resins. Further paint formulations were prepared using the conventional alkyd resin with different concentrations of diluent (expressed as % of the resin, i.e. 10% means 10% diluent to 90% resin)

Example T3

The data in Table 7 show that a VOC content of below 300 g/l can be achieved using the diluents of this invention at the 20% loading. Furthermore, the presence of the diluent in the paint had no effect (cf. the conventional white spirit-based paint) on the maximum film thickness which could be applied without the appearance of insightly wrinkles in the paint.

TABLE 7

| Diluent | Maximum film thickness* | VOC content** |
|---|---|---|
| AK1R 10% | 200 | 323 |
| AK1R 20% | 200 | 288 |
| White spirit | 200 | 366 |

*Expressed as bar coater gap width (microns)
**Volatile organic compound content, grammes per liter.

Tables 8 and 9 summarise the drying and hardness test data from the pigmented paint formulations based on conventional alkyd resins. The drying data in Table 8 show that the paints based on the reactive diluents of this invention dry in a period acceptable to the industry, even after storage at 35° C. for two weeks. Furthermore, the hardness of the paint films is excellent.

TABLE 8

| | Drying speeds | | | |
|---|---|---|---|---|
| Diluent | Drying Phase 2 * | Drying Phase 3 * | Drying Phase 2 ** | Drying Phase 3 ** |
| AK1R 10% | 3.5 | 5.5 | 4.5 | 7.5 |
| AK1R 20% | 4.5 | 6.0 | 5.4 | 7.1 |
| White spirit | 2.5 | 4.75 | 4.0 | 6.3 |

* After paint storage for 1 week at 23° C.
** After paint storage for 2 weeks at 35° C.

TABLE 9

| | (Hardness Data) | | | |
|---|---|---|---|---|
| Diluent Used | Indentation (microns) | | König hardness ** | |
| AK1R (10%) | 1.46* | 0.83# | 41@ | 46# |
| AK1R (20%) | 1.53* | 0.69# | 46@ | 51# |
| White spirit | 1.47* | 0.91# | 33@ | 35# |

*Film cured for 1 week at 23° C.
After 100 hours at 50° C.
@After 3 weeks at 23° C.
** In number of swings. Multiply by 1.4 to convert to seconds.

3.2 Tests of Clearcoats (Unpigmented Paints)

a) Methods Used to Prepare Unpigmented "Clearcoat" Formulations i) Materials Used Unpigmented ("clearcoat") paint formulations were prepared using the high solids alkyd resin SETAL® 293 described above in Section 3.1(a)(i). In addition to the diluent, Siccatol® 938 drier (ex AKZO NOBEL) and method ethyl ketone-oxime (hereafter "MEK-oxime") anti-skinning agent were used. Where used, the white spirit was Exxon type 100. The nominal proportions of the above materials in the paint formulations were:

TABLE 10

| Materials | Parts by weight |
|---|---|
| Resin + Diluent | 100.0 |
| Siccatol 938 | 6.7 |
| MEK-oxime | 0.5 |

Note that, for white spirit formulations only, the proportions of drier and antiskinning agent were calculated on the basis of the resin only. Thus, the concentration of these components in the paint was lower than for other diluents.

ii) Method of Preparation of Clearcoat Formulations

Alkyd resin and diluent were mixed in glass jars for 2 hours (eg using a Luckham multi-mix roller bed) in the proportions required to achieve a viscosity (measured via the ICI cone and plate method using a viscometer supplied by Research Equipment (London) Limited) of 0.68±0.03 Pa.s (6.8±0.3 poise). Typically, this resulted in a mixture which was ca. 80% w/w resin. If further additions of diluent or resin were required to adjust the viscosity to 0.68±0.03 Pa.s (6.8±0.3 poise), a further hour of mixing was allowed. The required quantity of drier was added and, after mixing (1 hour), the required amount of anti-skinning agent was added. After final mixing for at least 30 minutes, the viscosity of the mixture was measured to ensure that the viscosity was between 0.61 and 0.69 Pa.s (6.1 and 6.9 poise). The mixture ("formulation") was then divided into two tins and sealed so as to leave ca. 10–15% v/v headspace of air in the sealed jars. One of the tins was stored at 23° C. in darkness for 7 days before paint applications tests were performed. The second tin was stored ("aged") at 35° C. in daylight for 14 days before applications tests were performed.

b) Test Methods Used for Clearcoat Formulations i) Application of Paint Film

Thin films were applied to cleaned glass test plates using Sheen cube or draw-bar applicators with a nominal 75 μm gap width.

ii) Viscosity

The viscosity of each formulation was measured according to BS 3900 Part A7 with an ICI cone and plate viscometer (supplied by Research Equipment (London) Limited) at 23° C. and at a shear rate of 10,000 reciprocal seconds.

iii) Drying Performance

Drying performance was measured using films applied to 30 cm×2.5 cm glass strips and BK drying recorders. The BK recorders were enclosed in a Fisons controlled temperature and humidity cabinet so that the drying experiment could be performed at 10° C. and at 70% relative humidity. Sample performance was assessed on the basis of the dust drying time, T2.

iv) Incorporation of the Diluent into the Paint Film

An indication that the reactive diluent is incorporated into the paint film during the "cure", rather than undergoing evaporation, was obtained by monitoring the weight of the paint film following application. Weight measurements were done on a coating film applied with a 150 mm applicator on a glass substrate at 23° C. and 50%RH. The data are expressed as a % of the coated film weight, after the white spirit component of the siccative drier had evaporated (which took about 10 minutes).

NB. It is well known by those skilled in the art that day-to-day fluctuations in conditions can introduce some variability into experimental data. To minimise these errors, the tests presented below were conducted as follows: ca. five to ten paint formulations were prepared simultaneously and comprised one reference (white spirit) and four to nine reactive diluent-based paints. These samples were tested at the same time under identical conditions. Comparison of performance data from within these groups of formulations allowed errors due to random sources to be minimised.

c) Drying Speed Data from Clearcoats

The results in Tables 11 and 12 show that clearcoat paints based on the reactive diluents of the present invention reach the dust dry stage of drying within a period which is within about 4 hours of a traditional white spirit-based paint. These properties are regarded as satisfactory by the industry, and faster than that shown by the comparative examples.

TABLE 11

| Diluent Used | Drying times (hours) | |
| --- | --- | --- |
| | Paint stored for 1 week at 23° C. | Paint stored for 2 weeks at 35° C. |
| AK1 | 5.69 | 5.25 |
| AK2 | 6.25 | 7.16 |
| AK2R | 6.16 | 7.00 |
| AK2S | 5.58 | 5.21 |
| White spirit | 3.9 | 3.81 |

TABLE 12

| Diluent Used | Drying time (hours) | |
| --- | --- | --- |
| | Paint stored for 1 week at 23° C. | Paint stored for 2 weeks at 35° C. |
| AK1R | 4.9 | 5.2 |
| White spirit | 3.3 | 3.3 |

Weight measurements of two coated films are summarised in Table 13, and show that the diluent remains in the paint film, rather than evaporating.

TABLE 13

| Time (hours) | Reference (High solids resin + white spirit) | AK1 + high solids alkyd |
| --- | --- | --- |
| 0 | 100 | 100 |
| 0.5 | 97.99 | 97.28 |
| 1.0 | 98.31 | 97.34 |
| 5 | 102.22 | 100 |
| 24 | 100.64 | 99.41 |
| 72 | 98.91 | 99.31 |
| 195 | 97.28 | 100.03 |

What is claimed is:

1. A composition comprising a mixture of a fumarate, maleate, and 2-allyloxy-succinate esters of an alcohol selected from the group consisting of: 2-ethyl-hex-2-en-1-ol; 2-octen-1-ol; 1-octen-3-ol; 2,7-octadienol; hept-3-en-2-ol; 4-methyl pent-3-en-2-ol; 4-t-butoxy but-2-en-1-ol; 4-n-butoxy but-2-en-1-ol; cinnamyl alcohol; isophorol and mixtures thereof; said composition comprising 3–90 weight % fumarate, 0–50 weight % maleate and 10–97 weight % 2-allyloxy succinate.

2. A composition according to claim 1 which comprises 25–27 weight % fumarate, 0–5 weight % maleate and 25–75 weight % 2-allyloxy succinate.

3. A composition according to claim 1 which comprises either:
   i. di-(2,7-octadienyl)maleate
      di-(2,7octandienyl)fumarate and
      2-(2,7-octadienoxy)di-(2,7-octadienyl)succinate; or
   ii. di-(2-ethylhexenyl)maleate
      di-(2-ethylhexenyl)fumarate and
      2-(2-ethylhexenoxy)di-(2-ethylhexenyl)succinate.

4. A paint or coating formulation based on alkyd resins and comprising a mixture of esters comprising maleates, fumarates and 2-allyoxy succinates as defined in claim 1 as reactive diluents.

5. A paint or coating formulation based on alkyd resins according to claim 4 wherein said formulation also contains one or more of butylated hydroxy-toluene(2,6-butoxy-4-methyl phenol) and 2,4,6-tert-butyl phenol to inhibit haze and/or peroxidation.

6. Emulsion paints comprising vinyl acetate and a comonomer selected from the mixture of esters defined in claim 1.

7. A process for producing a mixture of fumarate, maleate and 2-allyloxy succinate esters (hereafter "MOE"), the 2-allyloxy succinate ester in said mixture being represented by formula (I);

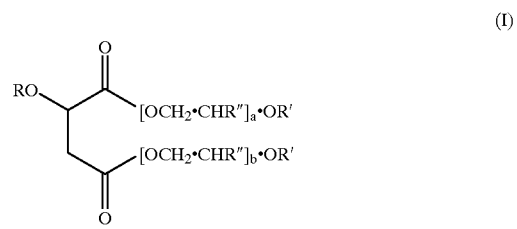

(I)

wherein each of a and b is the same or different and has a value of 0 or an integer from 1 to 6,

R=R'

R" is H or an alkyl or an alkylene group having 1 to 2 carbon atoms; and

R' is derived from an alcohol containing allylic unsaturation;

said process comprising reacting a dicarboxylic compound selected from the group consisting of maleic acid, maleic anhydride, fumaric acid and the dialkyl ester of maleic or fumaric acid with a reactant alcohol of the formula:

R'O[CHR"CH$_2$O]$_x$H wherein x is 0, or an integer of 1 to 6;
in the presence of a catalyst selected from the group consisting of:
   a. zinc acetate and
   b. a combination of
      (b1) one or more of dibutyl tin oxide, stannous oxide, zinc acetate, para-toluene sulphonic acid and phosphoric acid, and then
      (b2) an alkaline earth metal alkoxide.

8. A process according to claim 7, wherein R' is an allylic hydrocarbyl or an allylic hydrocarbyloxy alkylene group.

9. A process according to claim 7, wherein the reactant alcohol is selected from 2-ethyl-hex-2-en-1-ol; 2-octen-1-ol; 1-octen-3-ol; 2,7-octadienol; 2-ethyl allyl alcohol; hept-3-en-2-ol; 4-methyl pent-3-en-2-ol; 4-t-butoxy but-2-en-1-ol; 4-n-butoxy but-2-en-1-ol; cinnamyl alcohol; and isophorol.

10. A process according to claim 7 wherein the MOE is prepared by a single-stage or two stage reaction.

11. A process according to claim 10 wherein the MOE is prepared by a single stage reaction in which the dicarboxylic compound and the reactant alcohol are reacted at a temperature in the range from 80–140° C. in the presence of zinc acetate as catalyst.

12. A process according to claim 10 wherein the esterification is carried out using catalyst (b) in two stages; the first stage of which comprises reacting the reactant alcohol with maleic acid or anhydride and/or fumaric acid or esters thereof, in the presence of catalyst component (b1); and the second stage of which comprises reacting the purified reaction product of the first stage with a further aliquot of the reactant alcohol, in the presence of catalyst (b2).

13. A process according to claim 12 wherein the catalyst component (b1) is selected from dibutyl tin oxide, stannous oxalate, zinc acetate, para-toluene sulphonic acid or phosphoric acid and the first stage reaction is carried out at a temperature below 150° C.

14. A process according to claim 12, wherein the 2-allyloxy succinate ester content of the final MOE product is enhanced by carrying out the following steps upon completion of the first reaction stage:

stripping out unreacted materials by steam stripping or azeotropic distillation neutralizing or removing catalyst (b1), and filtering off solids from the reaction mixture to recover an initial MOE in the filtrate for reaction with said reactant alcohol in said second stage of reaction.

15. A process according to claim 7 wherein the alcohol reactant is used in a molar ratio of alcohol to dicarboxylic compound in the region of 2–4:1.

16. A process according to claim 7, wherein the alkaline earth metal in the alkoxide catalyst component (b2) is magnesium.

17. A process according to claim 7, wherein the reaction with the alkaline earth metal alkoxide is carried out at a temperature below 120° C. at pressures in the range from atmospheric to 50 Kpa.

* * * * *